(12) United States Patent
Choi

(10) Patent No.: US 10,980,516 B2
(45) Date of Patent: Apr. 20, 2021

(54) ULTRASONIC DIAGNOSTIC APPARATUS AND NON-TRANSITORY COMPUTER-READABLE MEDIUM

(71) Applicant: Toshiba Medical Systems Corporation, Otawara (JP)

(72) Inventor: Jaeho Choi, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 683 days.

(21) Appl. No.: 15/446,138

(22) Filed: Mar. 1, 2017

(65) Prior Publication Data

US 2017/0252013 A1 Sep. 7, 2017

(30) Foreign Application Priority Data

Mar. 1, 2016 (JP) .............................. JP2016-039111

(51) Int. Cl.
*A61B 8/00* (2006.01)
*A61B 8/14* (2006.01)
*A61B 8/08* (2006.01)

(52) U.S. Cl.
CPC .................. *A61B 8/54* (2013.01); *A61B 8/14* (2013.01); *A61B 8/467* (2013.01); *A61B 8/5207* (2013.01)

(58) Field of Classification Search
CPC ......... A61B 8/14; A61B 8/467; A61B 8/5207; A61B 8/54
See application file for complete search history.

(56) References Cited

U.S. PATENT DOCUMENTS

| 2004/0015079 | A1* | 1/2004 | Berger | A61B 8/546 600/437 |
| 2008/0112265 | A1* | 5/2008 | Urbano | G01S 7/52096 367/87 |

FOREIGN PATENT DOCUMENTS

| JP | 2003-245278 | 9/2003 |
| JP | 2005-103173 | 4/2005 |

* cited by examiner

*Primary Examiner* — Oommen Jacob
*Assistant Examiner* — Shahdeep Mohammed
(74) *Attorney, Agent, or Firm* — Oblon, McClelland, Maier & Neustadt, L.L.P.

(57) ABSTRACT

According to one embodiment, an ultrasonic diagnostic apparatus comprises plurality of processing circuitry and control circuitry. The control circuitry comprises a plurality of processing circuitry interfaces, a plurality of internal memories, and a control information interface. The plurality of processing circuitry interfaces respectively connected to the plurality of processing circuitry. The plurality of internal memory respectively connected to the plurality of processing circuitry interfaces. The control information interface configured to transfer control information associated with at least reception of the ultrasonic wave to at least one of the plurality of internal memories.

20 Claims, 9 Drawing Sheets

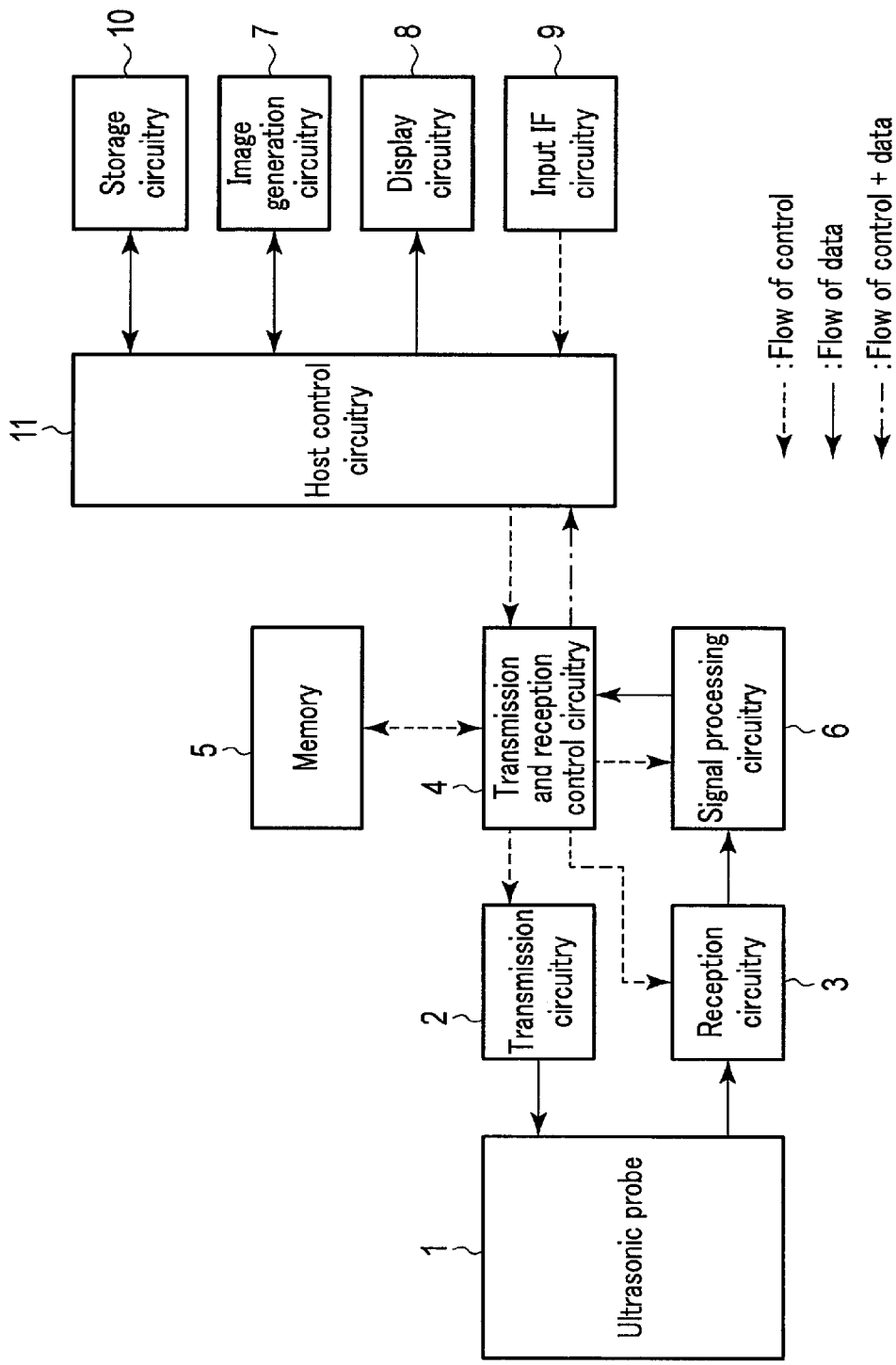
F I G. 1

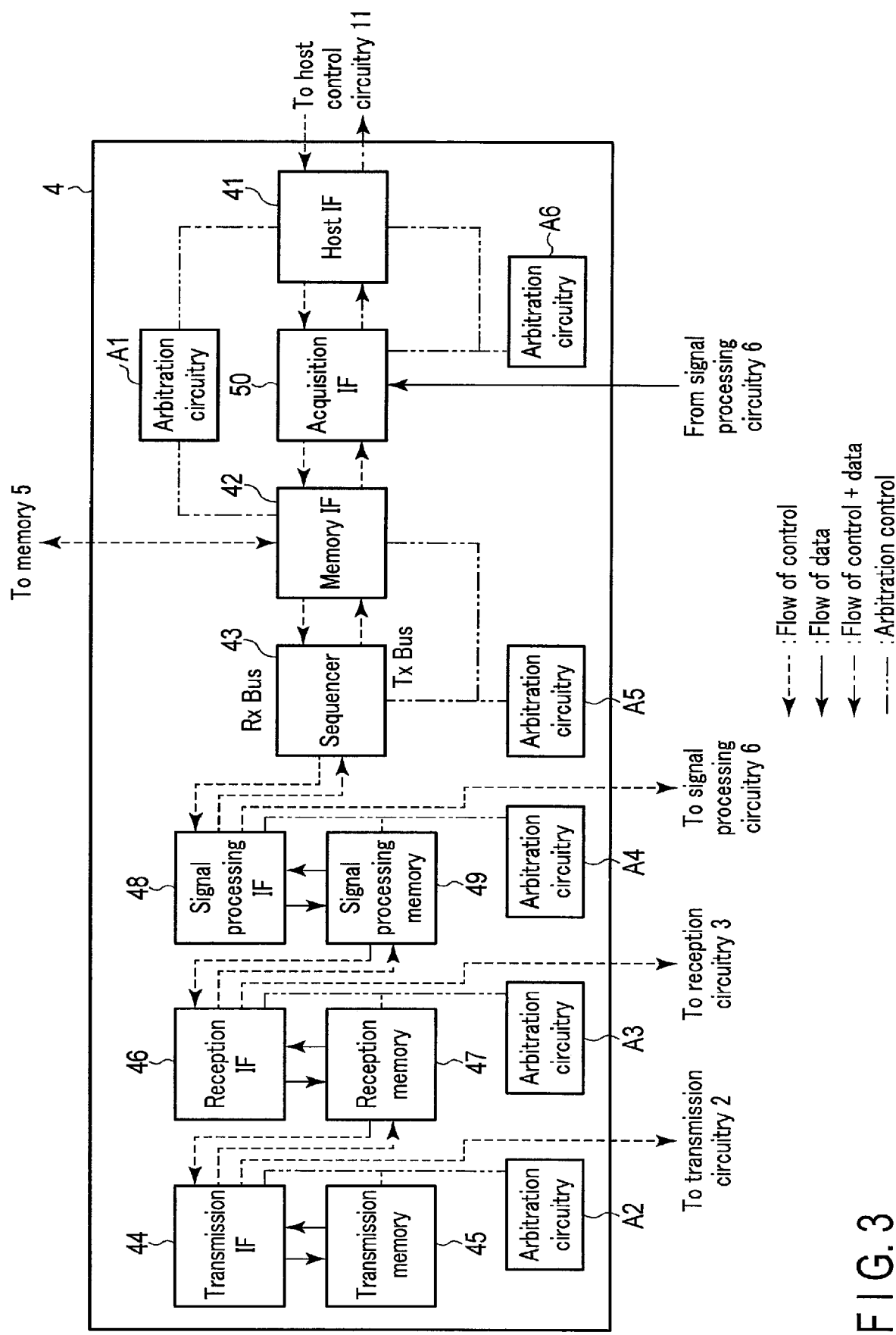
F I G. 3

| Current grant | Request | Grant to be given next (normal) | Grant to be given next (busy) |
|---|---|---|---|
| 00000 | 1xxxx | 10000 | 00000 |
| | x1xxx | 01000 | 01000 |
| | xx1xx | 00100 | 00000 |
| | xxx1x | 00010 | 00000 |
| | xxxx1 | 00001 | 00000 |
| 10000 | x1xxx | 01000 | 01000 |
| | xx1xx | 00100 | 00000 |
| | xxx1x | 00010 | 00000 |
| | xxxx1 | 00001 | 00000 |
| 01000 | 1xxxx | 10000 | 00000 |
| | xx1xx | 00100 | 00000 |
| | xxx1x | 00010 | 00000 |
| | xxxx1 | 00001 | 00000 |
| 00100 | 1xxxx | 10000 | 00000 |
| | x1xxx | 01000 | 01000 |
| | xxx1x | 00010 | 00000 |
| | xxxx1 | 00001 | 00000 |
| 00010 | 1xxxx | 10000 | 00000 |
| | x1xxx | 01000 | 01000 |
| | xx1xx | 00100 | 00000 |
| | xxxx1 | 00001 | 00000 |
| 00001 | 1xxxx | 10000 | 00000 |
| | x1xxx | 01000 | 01000 |
| | xx1xx | 00100 | 00000 |
| | xxx1x | 00010 | 00000 |

Correspondence with numbers
(host IF, memory IF, transmission IF, reception IF, signal processing IF)

F I G. 6

| Current grant | Request | Grant to be given next (normal) | Grant to be given next (busy) |
|---|---|---|---|
| 00000 | 1xxxx | 10000 | 00000 |
| | x1xxx | 01000 | 00000 |
| | xx1xx | 00100 | 00000 |
| | xxx1x | 00010 | 00000 |
| | xxxx1 | 00001 | 00000 |
| 10000 | x1xxx | 01000 | 00000 |
| | xx1xx | 00100 | 00000 |
| | xxx1x | 00010 | 00000 |
| | xxxx1 | 00001 | 00000 |
| 01000 | xx1xx | 00100 | 00000 |
| | xxx1x | 00010 | 00000 |
| | xxxx1 | 00001 | 00000 |
| | 1xxxx | 00010 | 00000 |
| 00100 | xxx1x | 00010 | 00000 |
| | xxxx1 | 00001 | 00000 |
| | 1xxxx | 10000 | 00000 |
| | x1xxx | 01000 | 00000 |
| 00010 | xxxx1 | 00001 | 00000 |
| | 1xxxx | 10000 | 00000 |
| | x1xxx | 01000 | 00000 |
| | xx1xx | 00100 | 00000 |
| 00001 | 1xxxx | 10000 | 00000 |
| | x1xxx | 01000 | 01000 |
| | xx1xx | 00100 | 00000 |
| | xxx1x | 00010 | 00000 |

Correspondence with numbers
(host IF, memory IF, transmission IF, reception IF, signal processing IF)

FIG. 8

ULTRASONIC DIAGNOSTIC APPARATUS AND NON-TRANSITORY COMPUTER-READABLE MEDIUM

CROSS-REFERENCE TO RELATED APPLICATIONS

This application is based upon and claims the benefit of priority from Japanese Patent Application No. 2016-039111, filed Mar. 1, 2016, the entire contents of which are incorporated herein by reference.

FIELD

Embodiments described herein relate generally to an ultrasonic diagnostic apparatus and a non-transitory computer-readable medium.

BACKGROUND

In general, processing associated with the transmission/reception of ultrasonic waves in an ultrasonic diagnostic apparatus is performed for each PRI (Pulse Repetition Interval) determined for each diagnosis mode in accordance with transmission/reception conditions. For example, this apparatus performs, for each PRI, the readout of control parameters stored in a memory such as a RAM (Random Access Memory), the transfer of the control parameters to corresponding devices, the transmission of ultrasonic waves based on the transferred control parameters, the reception of ultrasonic echo signals associated with the transmitted ultrasonic waves, and the signal processing of the received ultrasonic echo signals. Dedicated transmission and reception control circuitry controls processing associated with the transmission/reception of ultrasonic waves.

The above transmission and reception control circuitry shares an internal bus which transfers control parameters to corresponding devices. One arbitration circuitry included in the transmission and reception control circuitry manages the right of use of the internal bus according to round robin scheduling. Round robin scheduling is a scheme of sequentially giving the right of use of the internal bus to a plurality of control circuitry which attempt to transfer control parameters associated with the transmission/reception of ultrasonic waves by using the internal bus. For example, the transmission and reception control circuitry executes processing associated with the transmission/reception of ultrasonic waves in the order of transmission, reception, and signal processing. The transmission and reception control circuitry transfers control parameters necessary for each process associated with the transmission/reception of ultrasonic waves to corresponding devices by using the internal bus. That is, until the completion of the transfer of control parameters associated with one process, it is impossible to use the internal bus for the transfer of control parameters associated with other processes. In addition, it takes much time to transfer control parameters to an external bus with a low transfer rate, and it becomes impossible to complete the transfer of control parameters within a predetermined period included in a PRI. It is therefore necessary to prolong the PRI.

In addition, when simultaneously performing control parameter setting from a Host Central Processing Unit as a host device of the transmission and reception control circuitry as in TGC (Time Gain Control) parameter setting, the external bus becomes further busy, resulting in a decrease in the efficiency of transmission/reception control of ultrasonic waves. This leads to a decrease in frame rate and a deterioration in image resolution. In addition, as the number of ultrasonic transmission/reception channels increases, the transfer amount of control parameters increases. This imposes limitations on the amount of information which can be transferred by an ultrasonic diagnostic apparatus using conventional round robin scheduling.

BRIEF DESCRIPTION OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an ultrasonic diagnostic apparatus according to an embodiment;

FIG. 3 is a view showing the transfer flows of control parameters and data associated with at least reception of an ultrasonic wave in the transmission and reception control circuitry shown in FIG. 2;

FIG. 6 is a view showing the relationship between transfer requests from interfaces and transfer grants given to them in arbitration circuitry shown in FIG. 2;

FIG. 8 is a view showing the relationship between transfer requests from interfaces and transfer grants given to them in arbitration circuitry provided in the conventional transmission and reception control circuitry.

DETAILED DESCRIPTION

Figure 2:
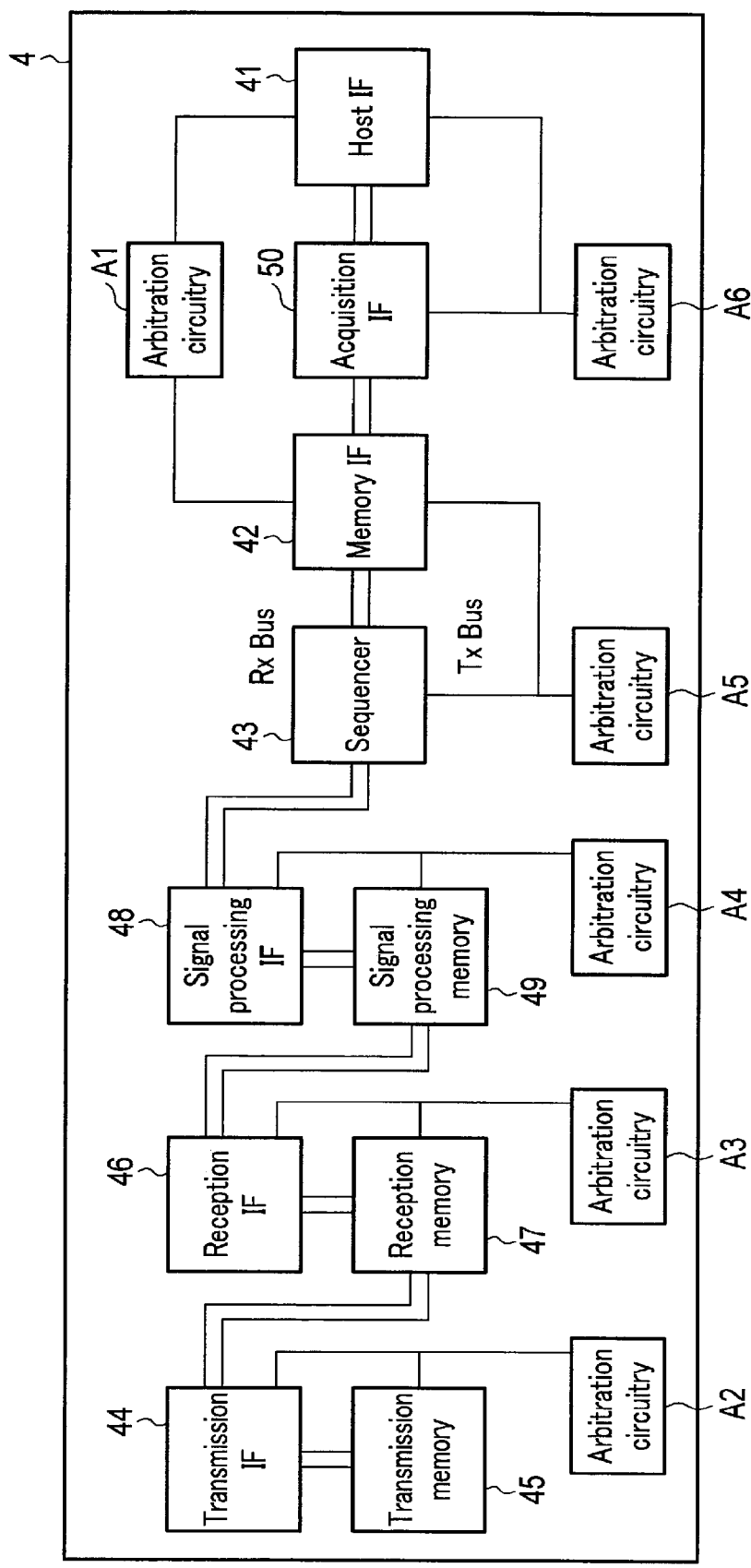
FIG. 2 is a block diagram showing the internal arrangement of transmission and reception control circuitry shown in FIG. 1.

In general, according to one embodiment, an ultrasonic diagnostic apparatus comprises plurality of processing circuitry and control circuitry. The plurality of processing circuitry configured to execute processing associated with at least reception of an ultrasonic wave. The control circuitry configured to control the plurality of processing circuitry. The control circuitry comprises a plurality of processing circuitry interfaces, a plurality of internal memory, and a control information interface. The plurality of processing circuitry interfaces respectively connected to the plurality of processing circuitry. The plurality of internal memories respectively connected to the plurality of processing circuitry interfaces. The control information interface configured to transfer control information associated with at least reception of the ultrasonic wave to at least one of the plurality of internal memories.

An ultrasonic diagnostic apparatus according to an embodiment will be described below with reference to the accompanying drawings.

FIG. 1 is a block diagram showing the arrangement of the ultrasonic diagnostic apparatus according to this embodiment. As shown in FIG. 1, the ultrasonic diagnostic apparatus includes, for example, an ultrasonic probe 1, transmission circuitry 2, reception circuitry 3, transmission and reception control circuitry 4, a memory 5, signal processing circuitry 6, image generation circuitry 7, display circuitry 8, IF circuitry (Input Interface circuitry) 9, storage circuitry 10, and host control circuitry 11.

The ultrasonic probe 1 converts a transmission signal supplied from the transmission circuitry 2 into an ultrasonic waves and transmits it to a subject. In addition, the ultrasonic probe 1 receives an ultrasonic echo signal reflected by the subject, converts it into an electrical signal, and outputs it to the reception circuitry 3. The transmission circuitry 2 is driven to transmit desired ultrasonic waves from the ultrasonic probe 1 in accordance with transmission parameters such as a PRF (Pulse Repetition Frequency), a transmission position, a transmission aperture, and a transmission delay, which are supplied from the transmission and reception control circuitry 4. The reception circuitry 3 generates beam data from an ultrasonic echo signal obtained by the ultrasonic probe 1 in accordance with reception parameters such as a reception element position, a reception aperture, a reception delay, and reception coordinates which are supplied from the transmission and reception control circuitry 4.

The transmission and reception control circuitry 4 is for example, an FPGA (Field Programmable Gate Array) for controlling transmission/reception processing circuitry which executes processing associated with the transmission/reception of ultrasonic waves. More specifically, the transmission and reception control circuitry 4 controls transmission/reception processing circuitry such as the transmission circuitry 2, the reception circuitry 3, and the signal processing circuitry 6 in accordance with an instruction from the host control circuitry 11. The transmission and reception control circuitry 4 determines a PRI corresponding to transmission/reception conditions for each diagnosis mode, and controls, for each PRI, transmission parameter transfer, reception parameter transfer, signal processing parameter transfer, ultrasonic waves transmission, and ultrasonic echo signal reception. In this case, diagnosis modes are, for example, B mode, B mode+C mode, B mode+PW mode, B mode+M mode, and CW mode. In addition, transmission/reception conditions are, for example, a change in depth of field in a scan target range, a change in the size of an ROI (Region of Interest), cursor movement, a change in acoustic power, and a change in scale. The transmission and reception control circuitry 4 transfers control parameters to the transmission/reception processing circuitry in accordance with transmission/reception conditions and the like instructed from the host control circuitry 11. A control parameter is a generic term indicating a transmission parameter, a reception parameter, and a signal processing parameter. The transmission and reception control circuitry 4 transfers transmission parameters such as a PRF, a transmission position, a transmission aperture, and a transmission delay to the transmission circuitry 2, stored in the memory 5 in accordance with a beam count, a frame count, a frame rate, a scan direction, a depth of field in a scan target range, and the like instructed by the host control circuitry 11. The transmission and reception control circuitry 4 also transfers reception parameters such as a reception element position, a reception aperture, a reception delay, and reception coordinates to the reception circuitry 3. In addition, the transmission and reception control circuitry 4 transfers signal processing parameters such as digital filter processing conditions to the signal processing circuitry 6. The transmission and reception control circuitry 4 also outputs processed data generated from beam data in the signal processing circuitry 6 to the image generation circuitry 7 via the host control circuitry 11.

Note that the transmission and reception control circuitry 4 may be implemented by at least one of an ASIC (Application Specific Integrated Circuit), a programmable logic device (for example, an SPLD (Simple Programmable Logic Device)), and a CPLD (Complex Programmable Logic Device).

The memory 5 is a RAM (Random Access Memory) storing, for example, control parameters for the respective transmission/reception processing circuitry. Control parameters stored in the memory 5 can be updated the host control circuitry 11. The memory 5 stores transmission parameters for the transmission circuitry 2, reception parameters for the reception circuitry 3, and signal processing parameters for the signal processing circuitry 6 which are set in accordance with information about various types of ultrasonic scan modes, the ultrasonic probe 1 to be connected, a parallel simultaneous reception count, and the like. For example, the memory 5 stores, as transmission parameters, transmission positions, transmission delays, and transmission apertures. In addition, the memory 5 stores, as reception parameters, reception element positions, reception apertures, reception delays, and reception coordinates. The memory 5 also stores digital filter coefficients as signal processing parameters. In addition, control parameters include substantive data and header information. Header information includes transfer destination addresses, and control parameters are transferred to transmission/reception processing circuitry corresponding to the transfer destination addresses.

The signal processing circuitry 6 generates processed data obtained by performing signal processing such as filtering processing for beam data output from the reception circuitry 3. The signal processing circuitry 6 outputs the generated processed data to the host control circuitry 11 via the transmission and reception control circuitry 4. Note that the signal processing circuitry 6 outputs processed data to the host control circuitry 11 via the transmission and reception control circuitry 4 according to a wiring scheme capable of transfer. However, a dedicated transfer path may be provided for transfer from the signal processing circuitry 6 to the host control circuitry 11. The image generation circuitry 7 scan-converts the processed data output from the host control circuitry 11 to generate a two-dimensional or three-dimensional ultrasonic image associated with a subject.

The display circuitry 8 displays an ultrasonic image generated by the image generation circuitry 7, various types of diagnosis parameters, and the like under the control of the host control circuitry 11. More specifically, the display circuitry 8 includes display interface circuitry and a display device. The display interface circuitry converts data representing a display target into a video signal. The display signal is supplied to the display device. The display device displays the video signal representing the display target. As a display device, for example, one of the following can be arbitrarily used: a CRT display (Cathode Ray Tube Display), an LCD (Liquid Crystal Display), an OELD (Organic Electra Luminescence Display), a plasma display, and another arbitrary display known in this technical field.

The input interface circuitry 9 is implemented by a trackball, switch buttons, a mouse, a keyboard, a touch pad which performs an input operation based on a touch on an operation surface, a touch panel display formed by integrating a display screen with a touch pad, and the like. The input interface circuitry 9 is an input device for setting various types of diagnosis modes and various types of control parameters accompanying the diagnosis modes to the ultrasonic diagnostic apparatus. The input interface circuitry 9 converts an input operation received from the operator into an electrical signal and outputs it to the host control circuitry 11. Note that in this embodiment, the input interface circuitry 9 is not limited to the one including physical operation components such as a trackball, switch buttons, a mouse, and a keyboard. For example, the input interface circuitry 9 includes electrical signal processing circuitry which receives an electrical signal corresponding to an input operation from an external input device provided separately from the apparatus and outputs the electrical signal to the host control circuitry 11.

The storage circuitry 10 includes, for example, an HDD (Hard Disk Drive) and an SSD (Solid State Drive) which can store a relatively large volume of data. For example, the storage circuitry 10 stores ultrasonic images supplied from the image generation circuitry 7 and additional information added to the ultrasonic images. Note that as the storage circuitry 10, a magneto-optical disk or an optical disk such as CD (Compact Disc) or DVD (Digital Versatile Disc) may be used other than a magnetic disk such as an HDD. In addition, a save area of the storage circuitry 10 may be located inside the ultrasonic diagnostic apparatus or an external storage device connected to the apparatus via a network.

The host control circuitry 11 executes control of the respective components of the ultrasonic diagnostic apparatus based on a diagnosis mode and various types of parameters set by the input interface circuitry 9. The host control circuitry 11 includes, as hardware resources, a processor such as a CPU or MPU (Micro Processing Unit) and memories such as a ROM (Read Only Memory) and RAM. The memory of the host control circuitry 11 stores an image acquisition program. The processor of the host control circuitry 11 executes control of the respective components of the ultrasonic diagnostic apparatus by executing the image acquisition program stored in the memory based on input signals from the input interface circuitry 9. For example, the host control circuitry 11 transfers control parameters based on input signals from the input interface circuitry 9 to the respective transmission/reception processing circuitry via the transmission and reception control circuitry 4. For example, to the reception circuitry 3 via the transmission and reception control circuitry 4, the host control circuitry 11 transfers, as such a control parameter, a TGC parameter for changing the TGC based on an input signal from the input interface circuitry 9.

(Internal Arrangement of Transmission and Reception Control Circuitry)

The internal arrangement of the transmission and reception control circuitry 4 according to this embodiment will be described below.

FIG. 2 is a block diagram showing the internal arrangement of the transmission and reception control circuitry 4 shown in FIG. 1. FIG. 3 is a view showing the transfer flows of control parameters and data associated with at least reception of an ultrasonic wave in the transmission and reception control circuitry 4 shown in FIG. 2. The transmission and reception control circuitry 4 includes a host side control information interface (a host IF) 41, a memory side control information interface (a memory IF) 42, a sequencer 43, a transmission circuitry interface (a transmission IF) 44, a transmission internal memory (a transmission memory) 45, a reception circuitry interface (a reception IF) 46, a reception internal memory (a reception memory) 47, a signal processing circuitry interface (a signal processing IF) 48, a signal processing internal memory (a signal processing memory) 49, a data acquisition interface (an acquisition IF) 50, and arbitration circuitry A1 to A6. The transmission and reception control circuitry 4 according to this embodiment has a function-specific circuitry arrangement having a transmission/reception processing circuitry interface, an internal memory, and arbitration circuitry provided for each function in the transmission/reception of ultrasonic waves.

In this case, for the sake of descriptive convenience, the host side control information interface 41 is written as the host IF 41, the memory side control information interface 42 as the memory IF 42, the transmission circuitry interface 44 as the transmission IF 44, the transmission internal memory 45 as the transmission memory 45, the reception circuitry interface 46 as the reception IF 46, the reception internal memory 47 as the reception memory 47, the signal processing circuitry interface 48 as the signal processing IF 48, the signal processing internal memory 49 as the signal processing memory 49, and the data acquisition interface 50 as the acquisition IF 50.

The host IF 41, the memory IF 42, the sequencer 43, the transmission IF 44, the transmission memory 45, the reception IF 46, the reception memory 47, the signal processing IF 48, the signal processing memory 49, and the acquisition IF 50 are connected via a common internal bus.

The host IF 41 is connected to the host control circuitry 11 via an external bus. The host IF 41 transfers in advance various types of control parameters transferred from the host control circuitry 11 to the memory 5 via the memory IF 42 before the start of the transmission/reception of ultrasonic waves by the ultrasonic diagnostic apparatus. The host IF 41 also transfers various types of control parameters transferred from the host control circuitry 11 to transmission/reception processing circuitry interfaces corresponding to the respective transmission/reception processing circuitry after the start of the transmission/reception of ultrasonic waves by the ultrasonic diagnostic apparatus.

The memory IF 42 is connected to the memory 5 via an external bus. The memory IF 42 transfers various types of control parameters stored in the memory 5 to internal memories corresponding to the respective transmission/reception processing circuitry. The memory IF 42 also transfers, to the host control circuitry 11, control parameter information transferred from the respective transmission/reception processing circuitry interfaces to the respective transmission/reception processing circuitry. Note that the memory IF 42 may be transfer various types of control parameters transferred from the host control circuitry 11 to transmission/reception processing circuitry interfaces corresponding to the respective transmission/reception processing circuitry.

The sequencer 43 determines a PRI in accordance with transmission/reception conditions for each diagnosis mode. The sequencer 43 transfers the determined PRI information to the host control circuitry 11.

The transmission IF 44 is connected to the transmission circuitry 2 via an external bus. The transmission IF 44 transfers transmission parameters stored in the transmission memory 45 to the transmission circuitry 2. The transmission IF 44 also transfers, to the transmission circuitry 2, transmission parameters transferred from the host IF 41.

The reception IF 46 is connected to the reception circuitry 3 via an external bus. The reception IF 46 transfers reception parameters stored in the reception memory 47 to the reception circuitry 3. The reception IF 46 also transfers, to the reception circuitry 3, reception parameters transferred from the host IF 41.

The signal processing IF 48 is connected to the signal processing circuitry 6 via an external bus. The signal processing IF 48 transfers signal processing parameters stored in the signal processing memory 49 to the signal processing circuitry 6. The signal processing IF 48 also transfers, to the signal processing circuitry 6, signal processing parameters transferred from the host IF 41.

The acquisition IF 50 is connected to the signal processing circuitry 6 via an external bus. The acquisition IF 50 transfers processed data generated by the signal processing circuitry 6 to the host control circuitry 11.

An internal bus from the host IF 41 to the transmission memory 45 will be referred to as an Rx bus. For example, the Rx bus is used to transfer control parameters from the memory IF 42 to each internal memory or used to transfer control parameters from the host IF 41 to each transmission/reception processing circuitry. In addition, an internal bus from the transmission memory 45 to the host IF 41 will be referred to as a Tx bus. For example, the Tx bus is used to transfer control parameters from each internal memory to a transmission/reception processing circuitry interface corresponding to each transmission/reception processing circuitry.

The arbitration circuitry A1 is connected to the host IF 41 and the memory IF 42. The arbitration circuitry A1 manages transfer requests for the transfer of control parameters to the respective transmission/reception processing circuitry interfaces by the host IF 41 via the internal bus and transfer requests for the transfer of control parameters to the respective internal memories by the memory IF 42 via the internal bus.

The arbitration circuitry A2 is connected to the transmission IF 44 and the transmission memory 45. The arbitration circuitry A2 manages transfer requests for the transfer of transmission parameters to the transmission IF 44 by the transmission memory 45 via the internal bus. The arbitration circuitry A3 is connected to the reception IF 46 and the reception memory 47. The arbitration circuitry A3 manages transfer requests for the transfer of reception parameters to the reception IF 46 by the reception memory 47 via the internal bus. The arbitration circuitry A4 is connected to the signal processing IF 48 and the signal processing memory 49. The arbitration circuitry A4 manages transfer requests for the transfer of signal processing parameters to the signal processing IF 48 by the signal processing memory 49 via the internal bus. The arbitration circuitry A5 is connected to the memory IF 42 and the sequencer 43. The arbitration circuitry A5 manages transfer requests for the transfer of PRI information to the host IF 41 by the sequencer 43 via the internal bus and the transfer of control parameter information by the memory IF 42 via the internal bus. The arbitration circuitry A6 is connected to the acquisition IF 50 and the host IF 41. The arbitration circuitry A6 manages transfer requests for the transfer of processed data to the host IF 41 by the acquisition IF 50 via the internal bus.

Note that the arbitration circuitry A1 to A6 manage the right of use of the internal bus according to round robin scheduling.

(Transfer of Control Parameters Associated with Transmission/Reception of Ultrasonic Waves in Transmission and Reception Control Circuitry)

The transfer of control parameters associated with the transmission/reception of ultrasonic waves in the transmission and reception control circuitry 4 will be described in detail below in consideration of the relationship between PRIs and the transfer of control parameters and arbitration control by the arbitration circuitry A1 to A4.

The transfer of control parameters transferred from the memory 5 will be described first. This embodiment will exemplify the transfer of control parameters in the second and subsequent PRIs from the start of the transmission/reception of ultrasonic waves.

Figure 4:
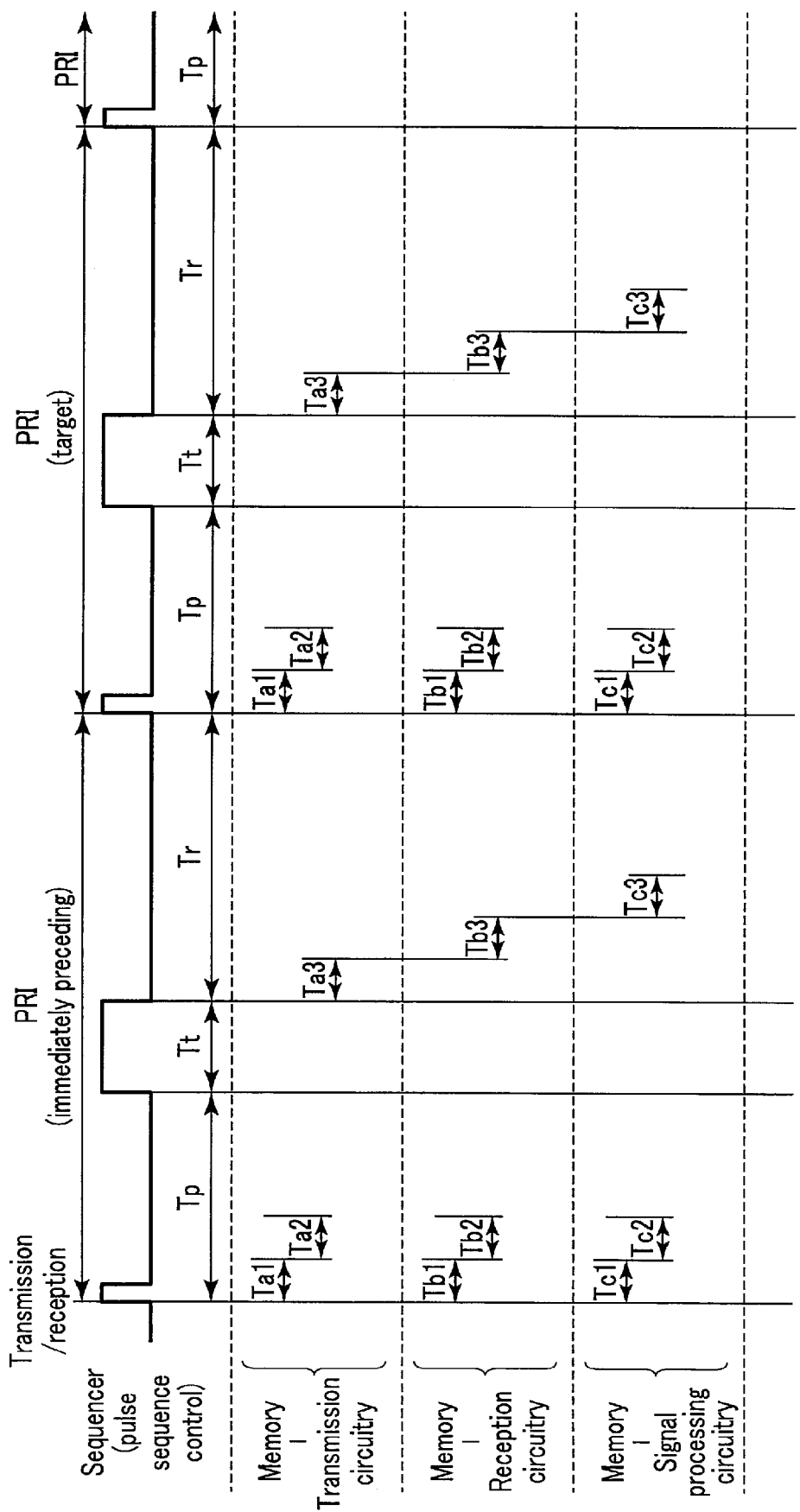
FIG. 4 is a chart showing a transfer sequence of control parameters from a memory with reference to a pulse repetition interval.

FIG. 4 is a chart showing a transfer sequence of control parameters from the memory 5 with reference to a PRI. As shown in FIG. 4, a PRI includes a transfer period Tp of control parameters to the respective transmission/reception processing circuitry, a transmission period Tt of ultrasonic waves, and a reception period Tr of ultrasonic echo signals.

A period Ta3 shown in FIG. 4 is a period in which transmission parameters to be transferred to the transmission circuitry 2 by the transmission IF 44 in the next PRI are transferred from the memory 5 to the transmission memory 45. A period Ta1 is a period in which the transmission parameters transferred to the transmission memory 45 are transferred to the transmission IF 44 by the transmission memory 45 via the internal bus. A period Ta2 is a period in which the transmission parameters transferred to the transmission IF 44 by the transmission memory 45 via the internal bus are transferred to the transmission circuitry 2 by the transmission IF 44 via the external bus.

A period Tb3 is a period in which reception parameters to be transferred to the reception circuitry 3 by the reception IF 46 in the next PRI are transferred from the memory 5 to the reception memory 47. A period Tb1 is a period in which the reception parameters transferred to the reception memory 47 are transferred to the reception IF 46 by the reception memory 47 via the internal bus. A period Tb2 is a period in which the reception parameters transferred to the reception IF 46 by the reception memory 47 via the internal bus are transferred to the reception circuitry 3 by the reception IF 46 via the external bus.

A period Tc3 is a period in which signal processing parameters to be transferred to the signal processing circuitry 6 by the signal processing IF 48 in the next PRI are transferred from the memory 5 to the signal processing memory 49. A period Tc1 is a period in which the signal processing parameters transferred to the signal processing memory 49 are transferred to the signal processing IF 48 by the signal processing memory 49 via the internal bus. A period Tc2 is a period in which the signal processing parameters transferred to the signal processing IF 48 by the signal processing memory 49 via the internal bus are transferred to the signal processing circuitry 6 by the signal processing IF 48 via the external bus.

In this case, before the start of the transmission/reception of ultrasonic waves in the ultrasonic diagnostic apparatus, control parameters transferred from the memory 5 by the memory IF 42 are stored in advance in a transfer target internal memory, of the plurality of internal memories, which corresponds to transfer target transmission/reception processing circuitry.

The arbitration circuitry A1 manages the transfer of control parameters from the memory 5 to each internal memory by the memory IF 42 in each PRI so as to complete the transfer before a PRI in which the control parameters are used. The arbitration circuitry A2 to A4 manage the transfer of control parameters to the respective transmission/reception processing circuitry by the respective internal memories and the transfer of control parameters to the respective transmission/reception processing circuitry by the respective transmission/reception processing circuitry interfaces in each PRI so as to complete the transfers before the transmission period Tt of ultrasonic signals in a PRI in which the control parameters are used.

In the common internal bus, until the transfer of control parameters associated with one process is complete, it is not possible to execute the transfer of control parameters associated with another process, and hence the arbitration circuitry A1 manages transfers so as to prevent the periods Ta3, Tb3, and Tc3 from overlapping.

The transfer of transmission parameters stored in the memory 5 will be described first.

In the period Ta3 in a PRI immediately preceding a PRI, in which the control parameters are used, the memory IF 42 supplies, to the arbitration circuitry A1, a transfer request for transmission parameters from the memory 5 to the transmission memory 45. The arbitration circuitry A1 outputs a transfer grant signal upon receiving the transfer request from the memory IF 42. In this case, a transfer grant from the arbitration circuitry is also called "giving a grant". For example, when the arbitration circuitry A1 gives a grant to the memory IF 42, the memory IF 42 can use the common internal bus and hence can transfer the transmission parameters from the memory 5 to the transmission memory 45. The memory IF 42 receives a transfer grant signal output from the arbitration circuitry A1, reads out transmission parameters from the memory 5, and transfers the transmission parameters to the transmission memory 45. In the period Ta1 in a PRI, in which the control parameters are used, the transmission memory 45 supplies, to the arbitration circuitry A2, a transfer request for transmission parameters to the transmission circuitry 2. The arbitration circuitry A2 receives the transfer request from the transmission memory 45, and outputs a transfer grant signal for granting the transfer of the transmission parameters to the transmission IF 44. Upon receiving the transfer grant signal output from the arbitration circuitry A2, the transmission memory 45 transfers transmission parameters to the transmission IF 44. In the period Ta2 in the PRI, in which the control parameters are used, the transmission IF 44 transfers, to the transmission circuitry 2, the transmission parameters transferred from the transmission memory 45 via the internal bus.

The transfer of reception parameters stored in the memory 5 will be described next.

In the period Tb3 in a PRI immediately preceding a PRI, in which the control parameters are used, the memory IF 42 supplies, to the arbitration circuitry A1, a transfer request for reception parameters from the memory 5 to the reception memory 47. Upon receiving the transfer request from the memory IF 42, the arbitration circuitry A1 outputs a transfer grant signal. Upon receiving a transfer grant signal output from the arbitration circuitry A1, the memory IF 42 reads out reception parameters from the memory 5, and transfers the reception parameters to the reception memory 47. In the period Tb1 in the PRI, in which the control parameters are used, the reception memory 47 supplies, to the arbitration circuitry A3, a transfer request for the reception parameters to the reception IF 46. Upon receiving a transfer request from the reception memory 47, the arbitration circuitry A3 outputs a transfer grant signal. Upon receiving the transfer grant signal output from the arbitration circuitry A3, the reception memory 47 transfers the reception parameters to the reception IF 46. In the period Tb2 in the PRI, in which the control parameters are used, the reception IF 46 transfers, to the reception circuitry 3, the reception parameters transferred by the reception memory 47 via the internal bus.

The transfer of signal processing parameters stored in the memory 5 will be described next.

In the period Tc3 in a PRI immediately preceding a PRI, in which the control parameters are used, the memory IF 42 supplies, to the arbitration circuitry A1, a transfer request for signal processing parameters from the memory 5 to the signal processing memory 49. Upon receiving the transfer request from the memory IF 42, the arbitration circuitry A1 outputs a transfer grant signal. Upon receiving the transfer grant signal output from the arbitration circuitry A1, the memory IF 42 transfers the signal processing parameters to the signal processing memory 49. In the period Tc1 in the PRI, in which the control parameters are used, the signal processing memory 49 supplies, to the arbitration circuitry A4, a transfer request for the signal processing parameters to the signal processing IF 48. Upon receiving the transfer request from the signal processing memory 49, the arbitration circuitry A4 outputs a transfer grant signal. Upon receiving the transfer grant signal output from the arbitration circuitry A4, the signal processing memory 49 reads out signal processing parameters from the memory 5, and transfers the signal processing parameters to the signal processing IF 48. In the period Tc2 in the PRI, in which the control parameters are used, the signal processing IF 48 transfers, to the signal processing circuitry 6, the signal processing parameters transferred by the signal processing IF 48 via the internal bus.

According to the above arrangement, in a period in a PRI immediately preceding a PRI in which the control parameter are used, the memory IF 42 according to this embodiment transfers in advance the control parameters to the internal memory corresponding to each transmission/reception processing circuitry interface. In addition, a transmission/reception processing circuitry interface, an internal memory, and arbitration circuitry are provided for each function in ultrasonic transmission/reception. This allows the respective internal memories to almost simultaneously transfer control parameters to the transmission/reception processing circuitry interfaces as transfer targets for the respective functions before a period in which the transfer target transmission/reception processing circuitry perform processing. It is possible to efficiently transfer, to transfer target transmission/reception processing circuitry interfaces, control parameters which have increased with an increase in the number of ultrasonic transmission/reception channels by almost simultaneously transferring the control parameters, thereby providing shorter PRIs. This can improve the diagnostic performance.

Referring to FIG. 4, in the period Tc2 in a PRI, in which the control parameters are used, signal processing parameters are transferred to the signal processing circuitry 6 only once. However, this is not exhaustive. For example, in the case of simultaneous reception, signal processing parameters may be read out and transferred by the number of times corresponding to the number of simultaneous beams.

The transfer of control parameters transferred from the host control circuitry 11 will be described next. This embodiment will exemplify the transfer of control parameters in the second and subsequent PRIs after the start of the transmission/reception of ultrasonic waves.

Figure 5:
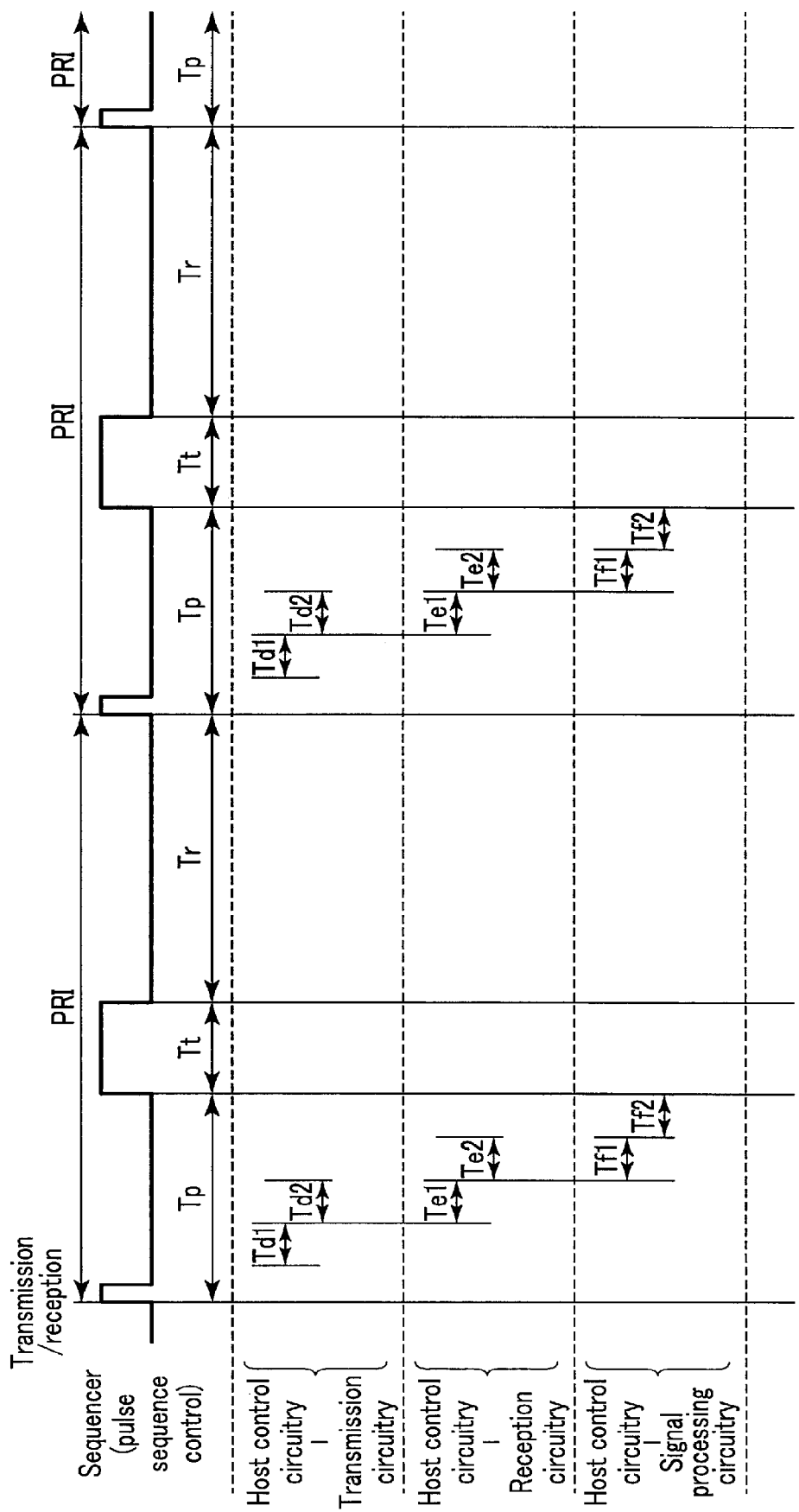
FIG. 5 is a timing chart showing the transfer sequence of control parameters from host control circuitry with reference to a pulse repetition interval.

FIG. 5 is a timing chart showing the transfer sequence of control parameters from the host control circuitry 11 with reference to a PRI. As shown in FIG. 5, each PRI includes a transfer period Tp for control parameters to the respective transmission/reception processing circuitry, a transmission period Tt for ultrasonic waves, and a reception period Tr for ultrasonic echo signals.

A period Td1 shown in FIG. 5 is a period in which transmission parameters to be transferred to the transmission circuitry 2 by the transmission IF 44 are transferred to the transmission IF 44 by the host IF 41 via the internal bus. A period Td2 is a period in which the transmission parameters transferred to the transmission IF 44 by the host IF 41 via the internal bus are transferred to the transmission circuitry 2 by the transmission IF 44 via the external bus. A period Te1 is a period in which reception parameters to be transferred to the reception circuitry 3 by the reception IF 46 are transferred to the reception IF 46 by the host IF 41 via the internal bus. A period Te2 is a period in which the reception parameters transferred to the reception IF 46 by the host IF 41 via the internal bus are transferred to the reception circuitry 3 by the reception IF 46 via the external bus. A period Tf1 is a period in which signal processing parameters to be transferred to the signal processing circuitry 6 by the signal processing IF 48 are transferred to the signal processing IF 48 by the host IF 41 via the internal bus. A period Tf2 is a period in which the signal processing parameters transferred to the signal processing IF 48 by the host IF 41 via the internal bus are transferred to the signal processing circuitry 6 by the signal processing IF 48 via the external bus.

The host IF 41 can transfer control parameters from the host control circuitry 11 to the respective transmission/reception processing circuitry interfaces at any time regardless of the periods of each PRI. In the common internal bus, until the transfer of control parameters associated with one process is complete, it is not possible to execute the transfer of control parameters associated with another process, and hence the arbitration circuitry A1 manages transfer so as to prevent the periods Td1, Te1, and Tf1 from overlapping. When the host IF 41 transfers control parameters from the host control circuitry 11 to the respective transmission/reception processing circuitry interfaces in a period (Ta3, Tb3, and Tc3 in FIG. 4) which almost coincides with the transfer of control parameters to the respective internal memories by the memory IF 42, the arbitration circuitry A1 manages the transfer to the respective transmission/reception processing circuitry interfaces so as to prevent them from overlapping each other. In addition, the arbitration circuitry A1 to A4 manage transfer so as to prevent the periods Ta1, Tb1, Tc1, Td1, Te1, and Tf1 from overlapping each other.

The transfer of transmission parameters from the host control circuitry 11 will be described first.

In the period Td1, the host IF 41 supplies, to the arbitration circuitry A1, a transfer request for the transmission parameters transmitted from the host control circuitry 11 to the transmission IF 44. Upon receiving the transfer request from the host IF 41, the arbitration circuitry A1 outputs a transfer grant signal. Upon receiving the transfer grant signal output from the arbitration circuitry A1, the host IF 41 transfers the transmission parameters to the transmission IF 44. In the period Td2, the transmission IF 44 transfers the transmission parameters transferred from the host IF 41 to the transmission circuitry 2.

The transfer of reception parameters transferred from the host control circuitry 11 will be described next.

In the period Te1, the host IF 41 supplies, to the arbitration circuitry A1, a transfer request for the reception parameters to the reception IF 46. Upon receiving the transfer request from the host IF 41, the arbitration circuitry A1 outputs a transfer grant signal. Upon receiving the transfer grant signal output from the arbitration circuitry A1, the host IF 41 transfers the reception parameters to the reception IF 46. In the period Te2, the reception IF 46 transfers, to the reception circuitry 3, the reception parameters transferred from the host IF 41.

The transfer of signal processing parameters transferred from the host control circuitry 11 will be described next.

In the period Tf1, the host IF 41 supplies, to the arbitration circuitry A1, a transfer request for the signal processing parameters to the signal processing IF 48. Upon receiving the transfer request from the host IF 41, the arbitration circuitry A1 outputs a transfer grant signal. Upon receiving the transfer grant signal output from the arbitration circuitry A1, the host IF 41 transfers the signal processing parameters to the signal processing IF 48. In the period Tf2, the signal processing IF 48 transfers, to the signal processing circuitry 6, the signal processing parameters transferred from the host IF 41.

(Transfer of Control Parameters Associated with Transmission/Reception of Ultrasonic Waves in Transmission and Reception Control Circuitry When Bus Busy Has Occurred)

The following is a case in which bus busy has occurred in the transfer of control parameters associated with ultrasonic transmission/reception in the transmission and reception control circuitry 4.

First of all, the transmission and reception control circuitry 4 uses arbitration control based on exception priority round robin scheduling. Exception priority round robin scheduling is a scheme of providing exceptional regulations under a predetermined condition in addition to the regulations provided by round robin scheduling. For example, at normal times, arbitration control is performed by round robin scheduling. When a busy signal is supplied from the reception IF 46 connected to an external bus with a low transfer rate, exceptional processing is executed. In addition, the highest priority is given to an interface which permits exceptions. For example, in the transmission and reception control circuitry 4 shown in FIG. 2, the highest priority is given to the memory IF 42. To give the highest priority is to give a grant to a specific interface regardless of whether a busy signal is supplied. For example, upon receiving a busy signal supplied from a transmission/reception processing circuitry interface connected to an external bus with a low transfer rate, the arbitration circuitry A1 always gives a transfer grant to a transfer request from the memory IF 42.

More specifically, the following description is based on the assumption that bus busy has occurred when a bus lower in transfer rate than other external buses is used as an external bus which connects the reception IF to the reception circuitry 3, and the reception IF 46 transfers control parameters to the reception circuitry 3. Assume that bus busy has occurred because the host IF 41 transfers reception parameters from the host control circuitry 11 to the reception IF 46 in a period almost coinciding with the transfer of reception parameters to the reception IF 46 by the reception memory 47.

FIG. 6 is a view showing the relationship between transfer requests from the respective interfaces and transfer grants to be given in the arbitration circuitry A1 to A4 shown in FIG. 2. FIG. 6 shows the association among current transfer grant information given by corresponding arbitration circuitry, interface information for the supply of transfer requests to the corresponding arbitration circuitry, interface information for the supply of transfer grants given by the arbitration circuitry corresponding to received transfer requests, and interface information for the supply of transfer grants by the corresponding arbitration circuitry upon reception of transfer requests during the occurrence of bus busy. The numbers of each set sequentially represent, from the left, the host IF 41, the memory IF 42, the transmission IF 44, the reception IF 46, and signal processing IF 48. In this case, "1" in FIG. 6 represents an interface which supplies a transfer request to corresponding arbitration circuitry or an interface to which a transfer grant is given by corresponding arbitration circuitry. "0" represents an interface to which no transfer grant is given by corresponding arbitration circuitry. "X" represents an interface set in either a state in which a transfer request is supplied to corresponding arbitration circuitry or a state in which no transfer request is supplied.

The current grant column shown in FIG. 6 represents interfaces to which current grants are given. In the current grant column, "00000" indicates that no transfer grant is currently given to any interfaces, "10000" indicates that the arbitration circuitry A1 has currently given a transfer grant to the host IF 41, "01000" indicates that the arbitration circuitry A1 has currently given a transfer grant to the memory IF 42, "00100" indicates that the arbitration circuitry A2 has currently given a transfer grant to the transmission IF 44, "00010" indicates that the arbitration circuitry A3 has currently given a transfer grant to the reception IF 46, and "00001" indicates that the arbitration circuitry A4 has currently given a transfer grant to the signal processing IF 48.

The request column shown in FIG. 6 represents interfaces which have supplied transfer requests. In the request column, "1XXXX" indicates that the host IF 41 has supplied a transfer request to the arbitration circuitry A1, and transfer requests from the remaining IFs each may be in either of the above states, "X1XXX" indicates that the memory IF 42 has supplied a transfer request to the arbitration circuitry A1, and transfer requests from the remaining IFs each may be in either of the above states, "XX1XX" indicates that the transmission IF 44 has supplied a transfer request to the arbitration circuitry A2, and transfer requests from the remaining IFs each may be in either of the above states, "XXX1X" indicates that the reception IF 46 has supplied a transfer request to the arbitration circuitry A3, and transfer requests from the remaining IFs each may be in either of the above states, and "XXXX1" indicates that the signal processing IF 48 has supplied a transfer request to the arbitration circuitry A4, and transfer requests from the remaining IFs each may be in either of the above states.

The "grant (normal) to be given next" column shown in FIG. 6 represents interfaces to which transfer grants have been given upon reception of transfer requests. In the "grant (normal) to be given next" column, "10000" indicates that the arbitration circuitry A1 gives a transfer grant to the host IF 41 in response to a transfer request from the host IF 41, "01000" indicates that the arbitration circuitry A1 gives a transfer grant to the memory IF 42 in response to a transfer request from the memory IF 42, "00100" indicates that the arbitration circuitry A2 gives a transfer grant to the transmission IF 44 in response to a transfer request from the transmission IF 44, "00010" indicates that the arbitration circuitry A3 gives a transfer grant to the reception IF 46 in response to a transfer request from the reception IF 46, and "00001" indicates that the arbitration circuitry A4 gives a transfer grant to the signal processing IF 48 in response to a transfer request from the signal processing IF 48.

The "grant (busy) to be given next" column shown in FIG. 6 represents interfaces to which transfer grants have been given upon reception of transfer requests at the occurrence of busy. In the "grant (busy) to be given next" column, "00000" indicates that no transfer grant is given to any interfaces at the occurrence of busy, and "01000" indicates that the arbitration circuitry A1 gives a transfer grant to the memory IF 42 in response to a transfer request from the memory IF 42 even at the occurrence of busy. In this embodiment, even at the occurrence of busy, the arbitration circuitry A1 can give a transfer grant to the memory IF 42 in response to a transfer request from the memory IF 42 even at the occurrence of busy.

The effects obtained by implementing an ultrasonic diagnostic apparatus according to the above embodiment will be described below in comparison with the conventional transmission and reception control circuitry.

Figure 7:
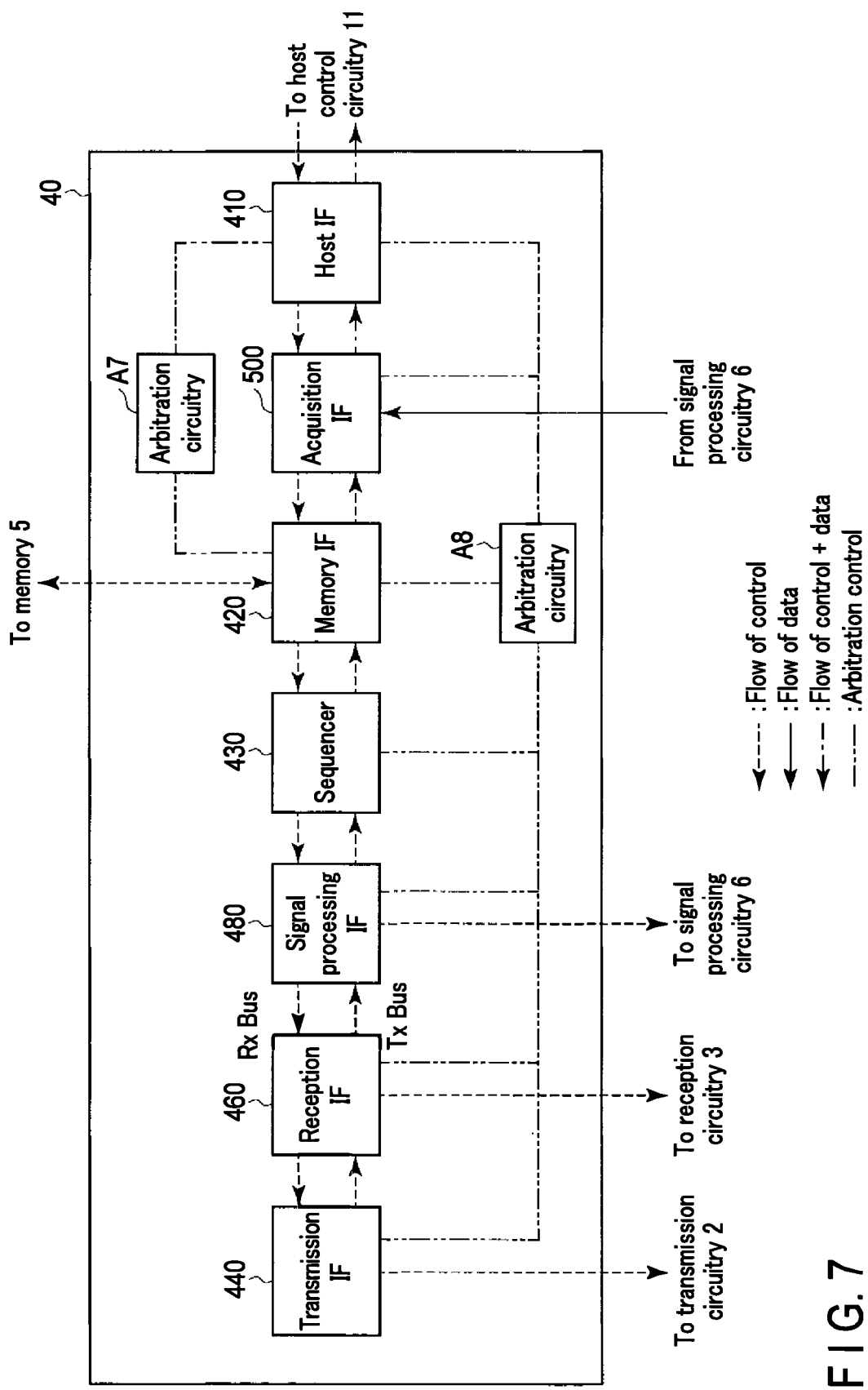
FIG. 7 is a block diagram showing the internal arrangement of conventional transmission and reception control circuitry.

FIG. 7 is a block diagram showing the internal arrangement of conventional transmission and reception control circuitry 40. FIG. 8 is a view showing the relationship between transfer requests from the respective interfaces in the arbitration circuitry provided in the transmission and reception control circuitry 40 and transfer grants given to the interfaces. The arbitration circuitry A7 and A8 each use arbitration control based on round robin scheduling without any exceptional regulations, unlike the transmission and reception control circuitry 4 shown in FIG. 2. The arbitration circuitry A7 and A8, each using the above round robin scheduling, equally give the right of use of the internal bus to each interface which supplies a transfer request. The order in which transfer grants are given to the respective interfaces when the respective interfaces simultaneously supply transfer requests is determined. For example, transfer grants are sequentially given to a host IF 410, a memory IF 420, a transmission IF 440, a reception IF 460, and a signal processing IF 480. In addition, all the transfer destinations of control parameters by the host IF 410 and the memory IF 420 are transmission/reception processing circuitry interfaces.

In the transmission and reception control circuitry 40 shown in FIG. 7, the memory IF 420 reads out reception parameters from the memory 5 and transfers the reception parameters to the reception IF 460. In an almost overlapping period, the host IF 410 transfers the reception parameters to the reception IF 460. Since an external bus with a low transfer rate is connected to the reception IF 460, bus busy is caused by the transfer of the reception parameters. When bus busy occurs, the reception IF 460 supplies a busy signal to the arbitration circuitry A7 to stop the transfer of the reception parameters. As shown in FIG. 8, in the conventional transmission and reception control circuitry 40, when the reception IF 460 connected to an external bus with a low transfer rate supplies a busy signal, the arbitration circuitry A7 using round robin scheduling cannot give a transfer grant to either the memory IF 420 or the host IF 410. As a result, each PRI needs to be prolonged.

The transmission and reception control circuitry 4 according to this embodiment is provided with the reception memory 47 corresponding to the reception IF 46 and the arbitration circuitry A3. In addition, assume that the transfer destination of reception parameters by the memory IF 420 is the reception memory 47. According to the above arrangement, since the host IF 41 differs from the memory IF 42 in the transfer destination of reception parameters, bus busy is difficult to occur. In addition, when the reception IF 46 transfers reception parameters to the reception circuitry 3, it is possible to manage the transfer of reception parameters by using the arbitration circuitry A3 so as to prevent the occurrence of bus busy.

In addition, the reception IF 46 is connected to an external bus with a low transfer rate, and the reception memory 47 transfers reception parameters to the reception IF 46 via a Tx bus in the transfer period Tp. Assume that in this case, the host IF 41 has transferred reception parameters to the reception IF 46. Since the external bus connected to the reception IF 46 has a low transfer rate, bus busy occurs. When bus busy occurs, the reception IF 46 supplies a busy signal to the arbitration circuitry A1. At this time, as shown in FIG. 6, the arbitration circuitry A1 using exception priority round robin scheduling can stop the transfer of reception parameters from the host IF 41 by not giving any transfer grant to the host IF 41. On the other hand, the arbitration circuitry A1 using exception priority round robin scheduling always gives a transfer grant with respect to a transfer request from the memory IF 42 having the highest priority. For this reason, even when a busy signal is supplied from the reception IF 460 connected to an external bus with a low transfer rate, the memory IF 42 can transfer reception parameters to the reception memory 47. This makes it possible to provide a PRI shorter than that provided by the transmission and reception control circuitry 40. This can improve the diagnostic performance.

(First Modification)

Figure 9:
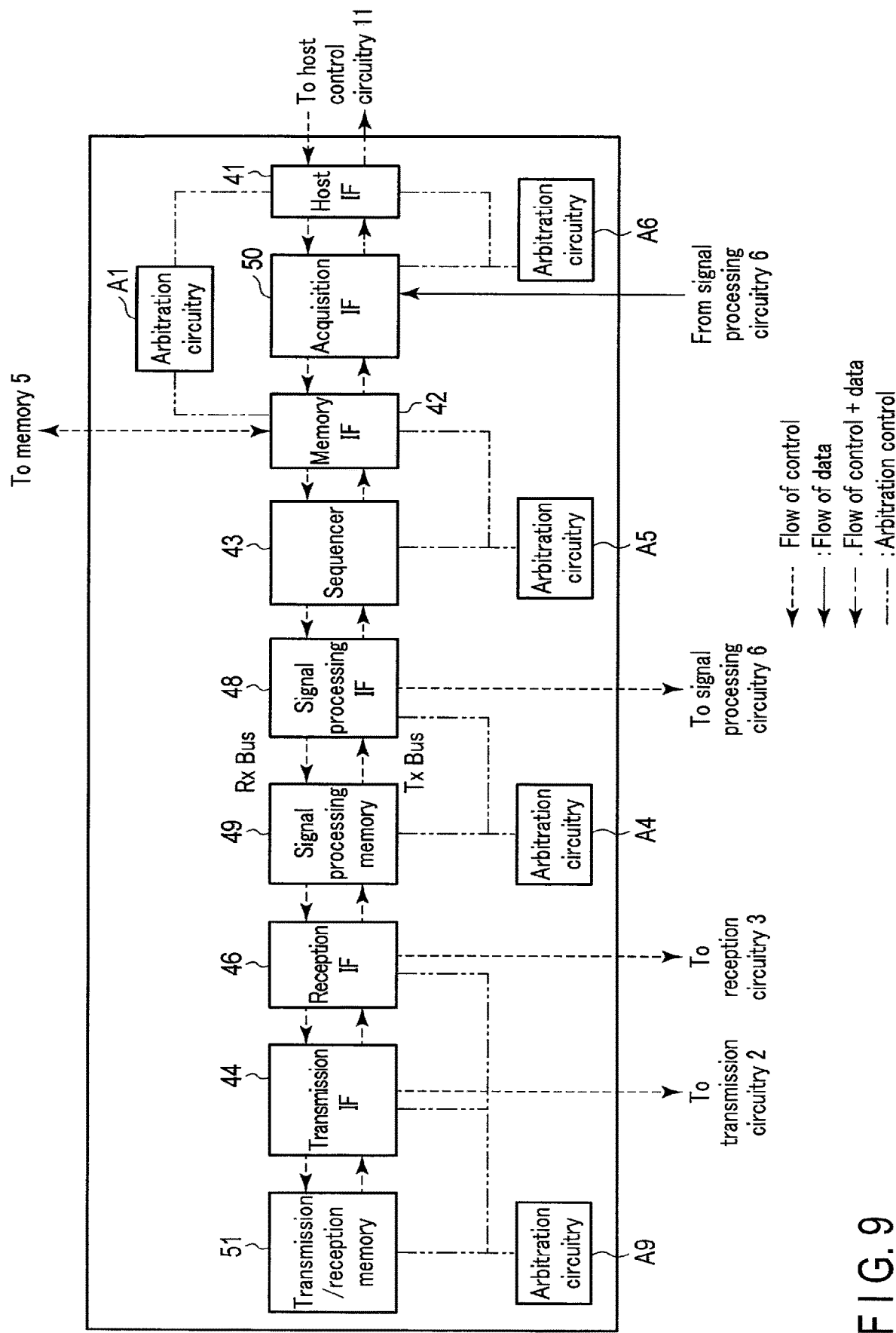
FIG. 9 is a block diagram showing a modification of the internal arrangement of the transmission and reception control circuitry according to this embodiment.

According to the above embodiment, in the transmission and reception control circuitry 4 shown in FIG. 2, the transmission IF 44, the transmission memory 45, and the arbitration circuitry A2 are provided for the transmission circuitry 2, and the reception IF 46, the reception memory 47, and the arbitration circuitry A3 are provided for the reception circuitry 3. However, this embodiment is not limited to this. FIG. 9 is a block diagram showing a modification of the internal arrangement of the transmission and reception control circuitry according to the embodiment. The transmission and reception control circuitry 4 shown in FIG. 9 may include a transmission/reception internal memory 51 and arbitration circuitry A9. The transmission/reception internal memory 51 is connected to the transmission circuitry 2 and the reception circuitry 3 via an internal bus. The arbitration circuitry A9 is connected to the transmission IF 44, the reception IF 46, and the transmission/reception internal memory 51. The arbitration circuitry A9 manages a transfer request for the transfer of transmission parameters to the transmission IF 44 by the transmission/reception internal memory 51 via the internal bus and a transfer request for the transfer of reception parameters to the reception IF 46 by the transmission/reception internal memory 51 via the internal bus.

For example, in the period Ta1 shown in FIG. 4, the transmission/reception internal memory 51 supplies, to the arbitration circuitry A9, a transfer request for transmission parameters to the transmission IF 44. Upon receiving the transfer request from the transmission/reception internal memory 51, the arbitration circuitry A9 outputs a transfer grant signal for granting the transfer of transmission parameters to the transmission IF 44. Upon receiving the transfer grant signal output from the arbitration circuitry A9, the transmission/reception internal memory 51 reads out transmission parameters from the memory 5, and transfers the transmission parameters to the transmission IF 44. In the period Ta2, the transmission IF 44 transfers, to the transmission circuitry 2, the transmission parameters transferred from the transmission/reception internal memory 51.

In the period Tb1 delayed by the period Ta1 shown in FIG. 4, the transmission/reception internal memory 51 supplies, to the arbitration circuitry A9, a transfer request for reception parameters to the reception IF 46. Upon receiving the transfer request from the transmission/reception internal memory 51, the arbitration circuitry A9 outputs a transfer grant signal. Upon receiving the transfer grant signal output from the arbitration circuitry A9, the transmission/reception internal memory 51 reads out reception parameters from the memory 5, and transfers the reception parameters to the reception IF 46. In the period Tb2 delayed by the period Ta1, the reception IF 46 transfers, to the reception circuitry 3, the reception parameters transferred from the transmission/reception internal memory 51.

(Second Modification)

In the above embodiment, the transfer destination of control parameters by the memory IF 42 via the internal bus is the internal memory corresponding to each transmission/reception processing circuitry interface, and the transfer destination of control parameters by the host IF 41 via the internal bus is each transmission/reception processing circuitry interface. However, this embodiment is not limited to this. The transmission and reception control circuitry 4 according to the embodiment may set the transfer destination of control parameters by the memory IF 42 via the internal bus to each transmission/reception processing circuitry interface, and the transfer destination of control parameters by the host IF 41 via the internal bus to the internal memory corresponding to each transmission/reception processing circuitry interface.

Overview

As described above, the ultrasonic diagnostic apparatus according to this embodiment includes the plurality of processing circuitry configured to execute processing associated with at least reception of an ultrasonic wave and the control circuitry configured to control the plurality of processing circuitry. The control circuitry includes the plurality of processing circuitry interfaces, the host side control information interface, and the plurality of internal memory. The processing circuitry interfaces respectively connected to the plurality of processing circuitry. The internal memory respectively connected to the processing circuitry interfaces. The control information interface configured to transfer control information associated with at least reception of the ultrasonic wave to at least one of the plurality of internal memories.

With the above arrangement, bus busy is difficult to occur in the ultrasonic diagnostic apparatus. This eliminates the necessity to prolong a PRI. This can improve the performance of the ultrasonic diagnostic apparatus. In addition, since the frame rate does not decrease, the diagnostic performance can be improved.

In this manner, the ultrasonic diagnostic apparatus according to this embodiment can achieve a high frame rate.

The term "predetermined processor" used in the above description indicates, for example, a dedicated or general-purpose processor, circuitry, processing circuitry, operation circuitry, arithmetic circuitry, ASIC (Application Specific Integrated Circuit), programmable logic device (for example, SPLD (Simple Programmable Logic Device or CPLD (Complex Programmable Logic Device), or FPGA (Field Programmable Gate Array). In addition, each constituent element (each processing circuitry) of this embodiment may be implemented by a plurality of processors as well as by a single processor. Furthermore, a plurality of constituent elements (a plurality of processing circuitry) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
a probe;
plurality of processing circuitry configured to execute processing associated with at least reception of an ultrasonic wave by the probe; and
control circuitry configured to control the plurality of processing circuitry,
wherein the control circuitry comprises
a plurality of processing circuitry interfaces respectively connected to the plurality of processing circuitry;
a plurality of internal memories respectively connected to the plurality of processing circuitry interfaces; and
a host side control interface configured to transfer control information associated with at least reception of the ultrasonic wave to at least one of the plurality of internal memories,
wherein the probe and control circuitry are separate devices,
the apparatus further comprising a memory configured to store the control information,
wherein the host side control interface transfers the control information stored in the memory to the at least one of the plurality of internal memories,
wherein at least one of the plurality of processing circuitry interfaces respectively connected to the plurality of internal memories transfers the control information transferred to the at least one of the plurality of internal memories to at least one of the plurality of processing circuitry respectively connected to the plurality of processing circuitry interfaces, and
wherein the control circuitry further comprises:
first arbitration circuitry configured to manage a transfer request issued by the host side control interface to transfer the control information from the memory to the at least one of the plurality of internal memories; and
second arbitration circuitry configured to manage a transmission request issued by the plurality of internal memories to transfer the control information to the at least one of the plurality of processing circuitry interfaces and a transfer request issued by the plurality of processing circuitry interfaces to transfer the control information to the at least one of the plurality of processing circuitry.

2. The apparatus of claim 1, wherein the control circuitry determines a predetermined pulse repetition interval including a period in which the control information is transferred from the memory to the at least one of the plurality of internal memories by the host side control interface, a period in which the control information is transferred to the at least one of the plurality of processing circuitry interfaces by the at least one of the plurality of internal memories, and a period in which the control information is transferred to the at least one of the plurality of processing circuitry by the at least one of the plurality of processing circuitry interfaces.

3. The apparatus of claim 2, wherein the plurality of processing circuitry include reception circuitry configured to execute processing associated with reception of the ultrasonic wave,
the memory stores a reception parameter as control information associated with the reception,
a processing circuitry interface associated with the reception of the plurality of processing circuitry interfaces transfers the reception parameter to the reception circuitry before a transmission period of the ultrasonic wave included in the pulse repetition interval,
the host side control interface transfers reception parameter from the memory to an internal memory associated with reception of the plurality of internal memories in a period until a start of next transmission/reception, and
the internal memory transfers the reception parameter transferred from the memory to the processing circuitry interface.

4. The apparatus of claim 2, wherein the plurality of processing circuitry include signal processing circuitry configured to execute predetermined signal processing associated with reception of the ultrasonic wave,
the memory stores a signal processing parameter as control information associated with the signal processing,
a processing circuitry interface associated with the signal processing of the plurality of processing circuitry interfaces transfers the signal processing parameter to the signal processing circuitry before a transmission period of the ultrasonic wave included in the pulse repetition interval,
the host side control interface transfers the signal processing parameter from the memory to an internal memory associated with signal processing of the plurality of internal memories in a period until a start of next transmission/reception, and
the internal memory transfers a reception parameter transferred from the memory to the processing circuitry interface.

5. The apparatus of claim 2, wherein the plurality of processing circuitry include transmission circuitry configured to execute processing associated with transmission of the ultrasonic wave,
the memory stores a transmission parameter as control information associated with the transmission,
a processing circuitry interface associated with the transmission of the plurality of processing circuitry interfaces transfers the transmission parameter to the transmission circuitry before a transmission period of the ultrasonic wave included in the pulse repetition interval,
the host side control interface transfers the transmission parameter from the memory to an internal memory associated with transmission of the plurality of internal memories in a period until a start of next transmission/reception, and
the internal memory transfers the transmission parameter transferred from the memory to the processing circuitry interface.

6. The apparatus of claim 1, wherein the host side control interface transfers in advance the control information to the at least one of the plurality of internal memories as a transfer target, which corresponds to the at least one of the plurality of processing circuitry as a transfer target, and
the at least one of the plurality of processing circuitry interfaces as the transfer target read the control information from the at least one of the plurality of internal memories as the transfer target before a processing period of the plurality of processing circuitry as the transfer target.

7. The apparatus of claim 6, wherein the first arbitration circuitry outputs a transfer grant signal for the control information from the memory to the at least one of the plurality of internal memories in response to a transfer request from the host side control interface after receiving a busy signal from a specific processing circuitry interface of the plurality of processing circuitry interfaces.

8. The apparatus of claim 7, further comprising host control circuitry connected to a user interface, wherein the host control circuitry is input control information by a user via the user interface,
   wherein the host side control interface transfers control information transferred from the host control circuitry to the at least one of the plurality of processing circuitry interfaces, and
   the at least one of the plurality of processing circuitry interfaces transfers the control information transferred from the host side control interface to the at least one of plurality of processing circuitry.

9. The apparatus of claim 8, wherein the first arbitration circuitry manages a transfer request for transfer of the control information input by the user to the at least one of the plurality of processing circuitry interfaces by the host side control interface.

10. The apparatus of claim 9, wherein the first arbitration circuitry outputs no transfer grant signal for the control information input by the user to the host side control interface in response to a transfer request from the host side control interface when a busy signal is supplied from a specific processing circuitry interface of the plurality of processing circuitry interfaces.

11. A non-transitory computer-readable medium which stores a control program for causing a computer including a plurality of processing circuitry configured to execute processing associated with at least reception of an ultrasonic wave of a probe to implement
   a host side control interface function of transferring control information for controlling at least one of plurality of processing circuitry to at least one of the plurality of internal memories within a control circuitry, and
   a processing circuitry interface function of transferring the control information stored in the at least one of the plurality of internal memories from the at least one of the plurality of internal memories to the at least one of plurality of processing circuitry,
   wherein the probe and control circuitry are separate devices, the computer further comprising a memory configured to store the control information,
   wherein the host side control interface transfers the control information stored in the memory to the at least one of the plurality of internal memories,
   wherein at least one of the plurality of processing circuitry interfaces respectively connected to the plurality of internal memories transfers the control information transferred to the at least one of the plurality of internal memories to at least one of the plurality of processing circuitry respectively connected to the plurality of processing circuitry interfaces, and
   wherein the control circuitry further comprises:
first arbitration circuitry configured to manage a transfer request issued by the host side control interface to transfer the control information from the memory to the at least one of the plurality of internal memories; and
   second arbitration circuitry configured to manage a transmission request issued by the plurality of internal memories to transfer the control information to the at least one of the plurality of processing circuitry interfaces and a transfer request issued by the plurality of processing circuitry interfaces to transfer the control information to the at least one of the plurality of processing circuitry.

12. The non-transitory computer-readable medium of claim 11, wherein the control circuitry determines a predetermined pulse repetition interval including a period in which the control information is transferred from the memory to the at least one of the plurality of internal memories by the host side control interface, a period in which the control information is transferred to the at least one of the plurality of processing circuitry interfaces by the at least one of the plurality of internal memories, and a period in which the control information is transferred to the at least one of the plurality of processing circuitry by the at least one of the plurality of processing circuitry interfaces.

13. The non-transitory computer-readable medium of claim 12, wherein
   the plurality of processing circuitry include reception circuitry configured to execute processing associated with reception of the ultrasonic wave,
   the memory stores a reception parameter as control information associated with the reception,
   a processing circuitry interface associated with the reception of the plurality of processing circuitry interfaces transfers the reception parameter to the reception circuitry before a transmission period of the ultrasonic wave included in the pulse repetition interval,
   the host side control interface transfers reception parameter from the memory to an internal memory associated with reception of the plurality of internal memories in a period until a start of next transmission/reception, and
   the internal memory transfers the reception parameter transferred from the memory to the processing circuitry interface.

14. The non-transitory computer-readable medium of claim 12, wherein the plurality of processing circuitry include signal processing circuitry configured to execute predetermined signal processing associated with reception of the ultrasonic wave,
   the memory stores a signal processing parameter as control information associated with the signal processing,
   a processing circuitry interface associated with the signal processing of the plurality of processing circuitry interfaces transfers the signal processing parameter to the signal processing circuitry before a transmission period of the ultrasonic wave included in the pulse repetition interval,
   the host side control interface transfers the signal processing parameter from the memory to an internal memory associated with signal processing of the plurality of internal memories in a period until a start of next transmission/reception, and
   the internal memory transfers a reception parameter transferred from the memory to the processing circuitry interface.

15. The non-transitory computer-readable medium of claim 12, wherein the plurality of processing circuitry include transmission circuitry configured to execute processing associated with transmission of the ultrasonic wave,
   the memory stores a transmission parameter as control information associated with the transmission,
   a processing circuitry interface associated with the transmission of the plurality of processing circuitry interfaces transfers the transmission parameter to the transmission circuitry before a transmission period of the ultrasonic wave included in the pulse repetition interval, the host side control interface transfers the transmission parameter from the memory to an internal memory associated with transmission of the plurality of internal memories in a period until a start of next transmission/reception, and the internal memory transfers the transmission parameter transferred from the memory to the processing circuitry interface.

16. The non-transitory computer-readable medium of claim 11, wherein the host side control interface transfers in advance the control information to the at least one of the plurality of internal memories as a transfer target, which corresponds to the at least one of the plurality of processing circuitry as a transfer target, and the at least one of the plurality of processing circuitry interfaces as the transfer target read the control information from the at least one of the plurality of internal memories as the transfer target before a processing period of the plurality of processing circuitry as the transfer target.

17. The non-transitory computer-readable medium of claim 16, wherein the first arbitration circuitry outputs a transfer grant signal for the control information from the memory to the at least one of the plurality of internal memories in response to a transfer request from the host side control interface after receiving a busy signal from a specific processing circuitry interface of the plurality of processing circuitry interfaces.

18. The non-transitory computer-readable medium of claim 17, wherein the computer further comprises host control circuitry connected to a user interface, wherein the host control circuitry is input control information by a user via the user interface, wherein the host side control interface transfers control information transferred from the host control circuitry to the at least one of the plurality of processing circuitry interfaces, and the at least one of the plurality of processing circuitry interfaces transfers the control information transferred from the host side control interface to the at least one of plurality of processing circuitry.

19. The non-transitory computer-readable medium of claim 18, wherein the first arbitration circuitry manages a transfer request for transfer of the control information input by the user to the at least one of the plurality of processing circuitry interfaces by the host side control interface.

20. The non-transitory computer-readable medium of claim 19, wherein the first arbitration circuitry outputs no transfer grant signal for the control information input by the user to the host side control interface in response to a transfer request from the host side control interface when a busy signal is supplied from a specific processing circuitry interface of the plurality of processing circuitry interfaces.

* * * * *